US008696675B2

(12) United States Patent
Boutin et al.

(10) Patent No.: US 8,696,675 B2
(45) Date of Patent: Apr. 15, 2014

(54) PROXIMITY-TRIGGERED COMPUTER-ASSISTED SURGERY SYSTEM AND METHOD

(75) Inventors: Yannick Boutin, Montréal (CA);
Jean-Guillaume Abiven, Montréal (CA); Mathieu Chevrier, Roxboro (CA)

(73) Assignee: Orthosoft Inc., Montreal (CA)

( * ) Notice: Subject to any disclaimer, the term of this patent is extended or adjusted under 35 U.S.C. 154(b) by 833 days.

(21) Appl. No.: 12/872,415

(22) Filed: Aug. 31, 2010

(65) Prior Publication Data

US 2012/0053488 A1 Mar. 1, 2012

(51) Int. Cl.
*A61F 2/46* (2006.01)
(52) U.S. Cl.
USPC .......................................... 606/86 R; 600/587
(58) Field of Classification Search
USPC .................................................. 606/86 R, 87
See application file for complete search history.

(56) References Cited

U.S. PATENT DOCUMENTS

| 6,434,507 | B1 * | 8/2002 | Clayton et al. ................ 702/152 |
| 6,946,956 | B2 | 9/2005 | Hayashi et al. |
| 6,954,148 | B2 | 10/2005 | Pulkkinen et al. |
| 2003/0078494 | A1 | 4/2003 | Panescu et al. |
| 2006/0155291 | A1 * | 7/2006 | Farrar et al. ..................... 606/87 |
| 2010/0063508 | A1 * | 3/2010 | Borja et al. ..................... 606/88 |

\* cited by examiner

*Primary Examiner* — Nicholas Woodall
(74) *Attorney, Agent, or Firm* — Norton Rose Fulbright Canada LLP

(57) ABSTRACT

A computer-assisted surgery system comprises a first surgical device with a tracking unit tracked during a surgical procedure and adapted to perform a first function associated to the surgical procedure. A second surgical device is adapted to perform a second function associated to the surgical procedure. A triggered unit is triggered when the first surgical device and the second surgical device reach a predetermined proximity relation. A surgical procedure processing unit tracks the first surgical device. A trigger detector detects a triggering of the triggered unit. A CAS application operates steps of a surgical procedure. A controller commands the CAS application to activate a selected step associated with the second function in the surgical procedure when the trigger detector signals a detection. An interface displays information about the selected step in the surgical procedure.

9 Claims, 4 Drawing Sheets

PROXIMITY-TRIGGERED COMPUTER-ASSISTED SURGERY SYSTEM AND METHOD

FIELD OF THE APPLICATION

The present application relates to computer-assisted surgery, and more particularly to surgical tools used in computer-assisted surgery and triggering associated therewith.

BACKGROUND OF THE ART

Computer-assisted surgery has evolved over the years to use the computational speed of computers to guide surgeons and operating-room personnel in performing orthopedic procedures on the bones with high degrees of precision and accuracy. In order to lessen the requirements of hardware in the operating room, microelectromechanical systems (MEMS) such as gyroscopes and accelerometers are used in calculating orientation and/or position of surgical tools and bones.

MEMS are used in addition or as an alternative to other types of trackers, such as optical tracking systems (e.g., Navitrack™). In some cases, optical tracking systems can be replaced with MEMS, therefore removing bulky optical tracker devices on tools and bones. Because of the minute format of MEMS, it is even contemplated to perform computer-assisted surgery without a self-standing monitor, by instead providing all information within the surgical field with LED indicators or screens on tools. It is desirable to automate computer-assisted surgery using MEMS to accelerate surgical procedures.

SUMMARY OF THE APPLICATION

Therefore, in accordance with the present application, there is provided a computer-assisted surgery system comprising: a first surgical device with a tracking unit tracked during a surgical procedure and adapted to perform a first function associated to the surgical procedure; a second surgical device adapted to perform a second function associated to the surgical procedure; a triggered unit triggered when the first surgical device and the second surgical device reach a predetermined proximity relation; a surgical procedure processing unit tracking at least the first surgical device, the surgical procedure processor comprising a trigger detector detecting a triggering of the triggered unit, a computer-assisted surgery application operating steps of a surgical procedure, a controller for commanding the computer-assisted surgery application to activate a selected step associated with the second function in the surgical procedure when the trigger detector signals a detection, and an interface for displaying information about the selected step in the surgical procedure.

Further in accordance with the present application, there is provided a method for progressing through steps of a surgical procedure of a computer-assisted surgery application, comprising: tracking at least a first surgical device adapted to perform a first function associated with the surgical procedure; detecting a predetermined proximity relation between the first surgical device and a second surgical device adapted to perform a second function associated with the surgical procedure; activating a selected step of the surgical procedure associated with the second function when the predetermined proximity relation is detected; and displaying information related to the selected step.

DESCRIPTION OF THE EXEMPLARY EMBODIMENTS

Figure 1:
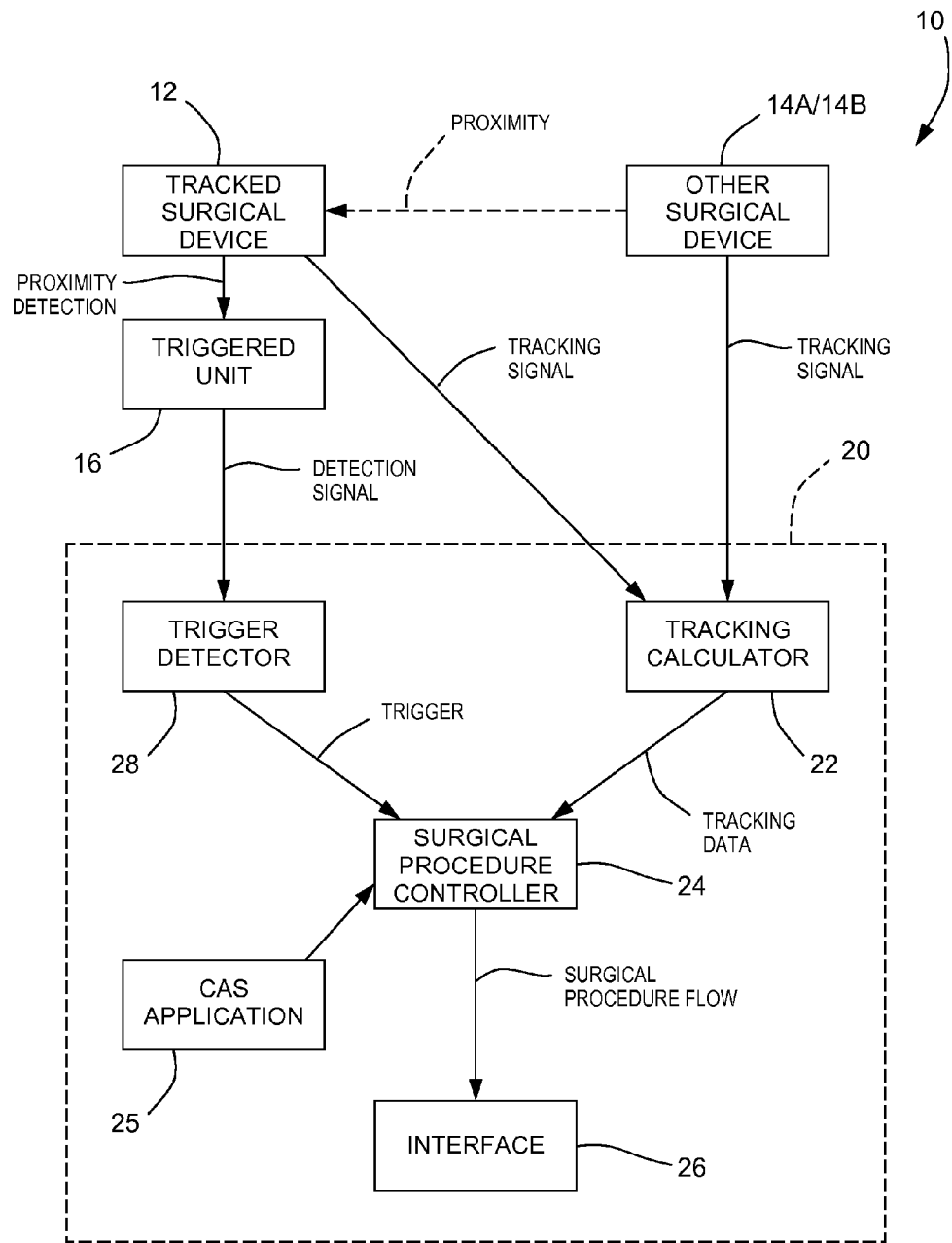
FIG. 1 is a block diagram of a proximity-triggered computer-assisted surgery system in accordance with an exemplary embodiment of the present application.

Referring to the drawings, and more particularly to FIGS. 2, 3, 4A and 4B, there is illustrated a lower leg of a patient, with soft tissue removed so as to expose an upper end of the tibia A, for use with a proximity-triggered computer-assisted surgery system of the exemplary embodiment. Although the computer-assisted surgery system and associated method are described and illustrated as used for tibial alterations during knee-replacement surgery, it is understood that the proximity-triggered computer-assisted surgery system and method of the present embodiment may be used in all other types of orthopedic surgery, such as total knee replacement, total hip replacement, spine surgery, or any other type of orthopedic surgery requiring surgical devices as described for the exemplary embodiment.

Referring to FIG. 1, the proximity-triggered computer-assisted surgery (CAS) system is generally shown at 10. The CAS system 10 may feature a plurality of surgical devices. In the illustrated embodiment, the CAS system 10 has a tracked surgical device 12 that is secured to a bone. In the exemplary embodiment of FIG. 1, the tracked surgical device 12 is a MEMS-operated reference unit that is secured to the bone so as to provide tracking data (i.e., orientation and/or position information) related to the bone A through various calibration and referencing steps.

Figure 2:
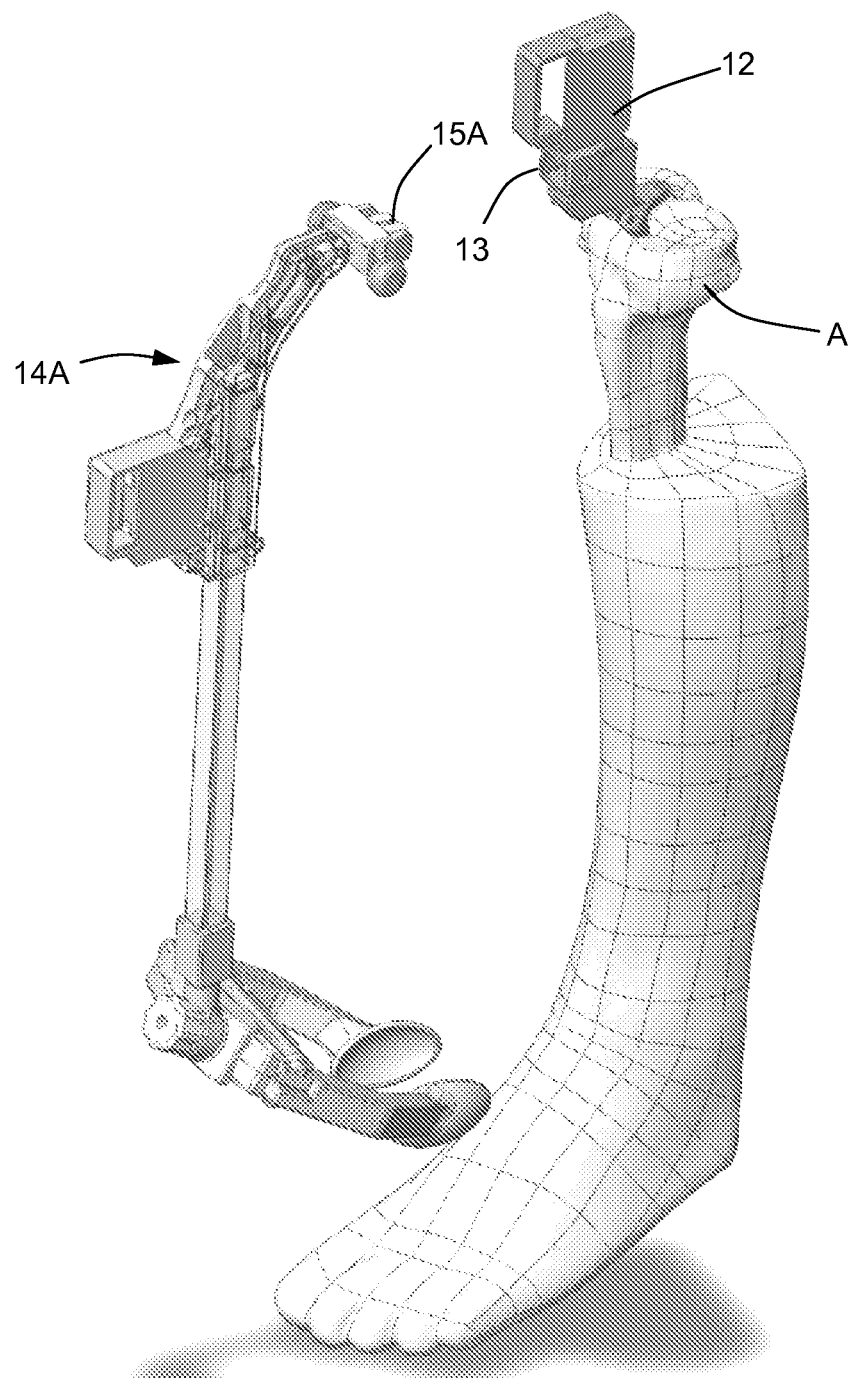
FIG. 2 is a schematic view of mating surgical devices with respect to a bone, as used with the computer-assisted surgery system of FIG. 1.
Figure 3:
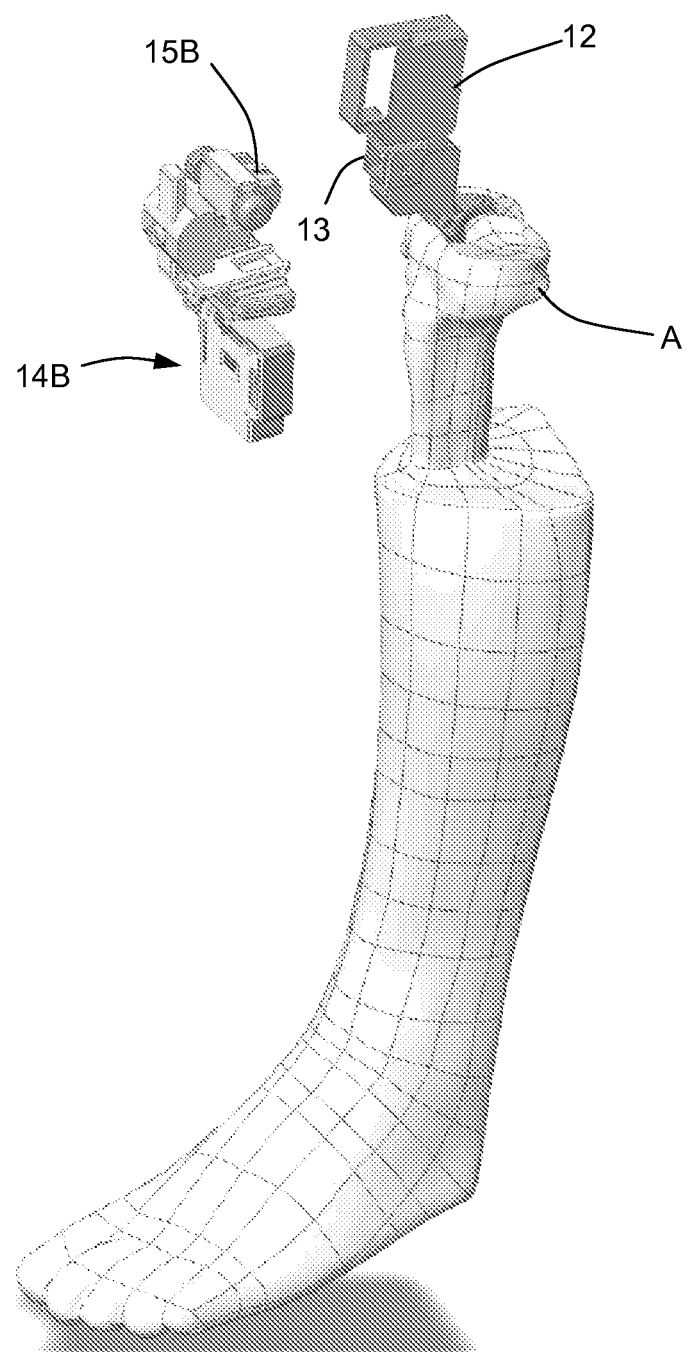
FIG. 3 is a schematic view of mating surgical devices with respect to a bone, as used with the computer-assisted surgery system of FIG. 1.

As shown in FIGS. 2 and 3, the tracked surgical device 12 is a tibial reference secured to an upper end of the tibia A, so as to act as a tracking reference. The tibial reference 12 has a female connector 13 in order to receive other surgical devices therein. In one embodiment, other surgical devices in mating engagement with the tracked surgical device 12 will also be tracked by the geometrical relation between the tracked surgical device 12 and the other surgical device. In FIG. 2, the other surgical device is illustrated at 14A and is known as a tibial digitizer. In FIG. 3, the other surgical device 14B is a cutting block. The tibial digitizer and the cutting block respectively have male connectors 15A and 15B.

In the exemplary embodiment, the tracked surgical device 12 has electronic circuitry, as it operates MEMS to provide the tracking data. A triggered unit 16 (FIG. 1) is provided on the tracked surgical device 12, for instance as part of the electronic circuitry, so as to be triggered when a mating engagement is completed between the female connector 13 of the tracked surgical device 12 and the male connector 15 of the other surgical device 14. The triggered unit 16 may be any one of a plurality of units. For instance, the triggered unit 16 may be a simple switch that is provided in the female connector 13 so as to be triggered by the contact with the male connector 15. Other alternatives include a magnet and appropriate sensor, respectively in opposite devices, proximity switches and sensors, a conductive element and an open circuit in opposite devices, or any other appropriate type of triggered unit or switch.

The proximity-triggered CAS system 10 features a proximity-triggered CAS processing unit 20 that comprises a tracking calculator 22 in order to track the surgical device and the surgical devices 14A/14B through the connected relation with the surgical device 12, or independently therefrom of the surgical device 14A/14B have their own MEMS. The tracking calculator 22 receives tracking signals from the MEMS of the surgical devices and converts the data with prior calibration and referencing information into tracking values related to the surgical devices 12, 14A and/or 14B, as well as related to the bone A or any other appropriate bone that has been calibrated and referenced as well.

A surgical procedure controller 24 operates a CAS application 25 that guides the surgeon and personnel of the operating room in following a series of manual steps according to the CAS application to define bone axes, tool axes, models, as well as in providing surgical step information, to guide surgical operations on the bones. The CAS application 25 follows a specific flow of steps according to the information entered by the operator of the CAS system 10, as well as through the tracking data provided by the tracking calculator 22. The resulting information is displayed on an interface 26, typically a monitor of a self-standing station, or screen or LED indicators directly on the surgical devices.

A trigger detector 28 is provided in the CAS processing unit 20 so as to receive a detection signal from the triggered unit 16. Upon receiving the detection signal, the trigger detector 28 signals the triggering to the surgical procedure controller 24. The trigger detector 28 may perform a confirmation step, for instance by confirming that the surgical device 14 is sufficiently close to the surgical device 12, when proximity sensors are used. Moreover, if the devices 12 and 14 matingly engage, the trigger detector 28 may require a sustained detection signal to confirm the triggering. These confirmation steps may be performed by the triggered unit 16 as well, in both case by the presence of a conditions database.

The triggering is automatic further to the positioning of the surgical device 14 in proximity to or in contact with the surgical device 12. Accordingly, the surgical procedure controller 24 will alter its flow of operations following the receipt of a signal from the trigger detector 28 to further advance the flow of steps of the surgical procedure, as observed on the interface 26, for instance by the change of data on the screen. Accordingly, by performing this action, one step of interfacing between the operator and the CAS system 10 is removed, and replaced by an intuitive step required in most standard surgical techniques for a given type of procedure.

Figure 4A:
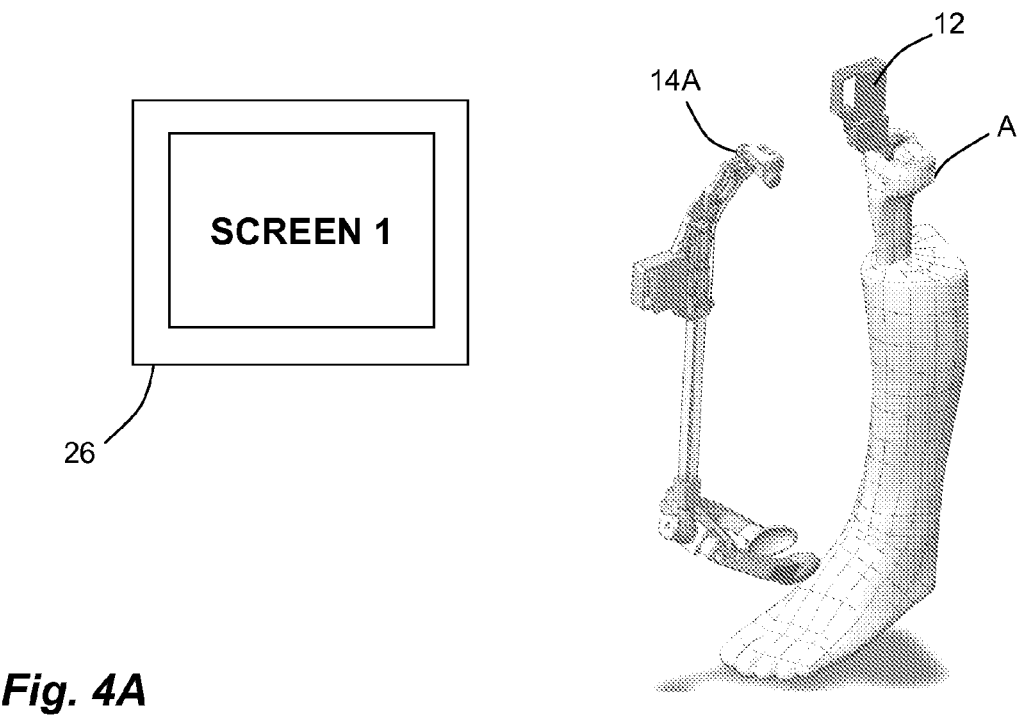
FIG. 4A is a schematic view of the mating surgical devices of FIG. 2 with a CAS monitor, prior to mating.
Figure 4B:
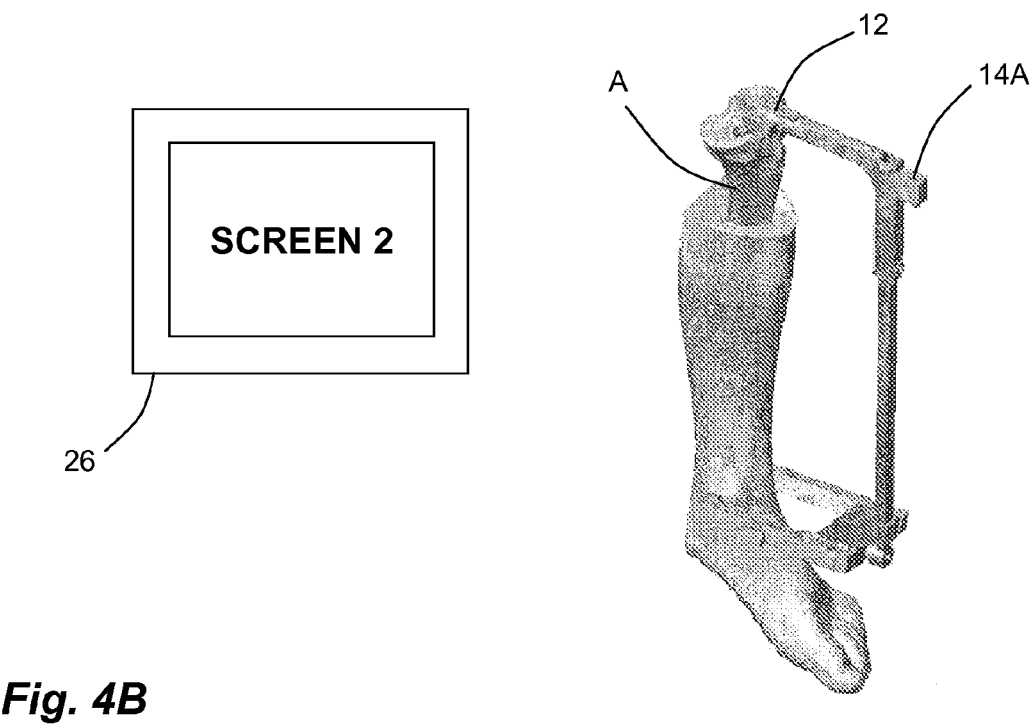
FIG. 4B is a schematic view of the mating surgical devices of FIG. 2 with the CAS monitor, after mating.

Referring to FIGS. 4A and 4B, there is illustrated the method of automatically triggering the CAS system by proximity. In FIG. 4A, the tibial reference 12 is secured to the tibia A, and is calibrated and referenced. Accordingly, the tibia A is tracked for subsequent surgical steps thereon.

The interface 26 shows screen 1, in accordance with the progress that is made in the surgical procedure. Screen 1 may therefore display tracking information (e.g., axes, bone models, values) pertaining to the bone A from the tracking of the tibial reference 12. Moreover, according to the surgical procedure, screen 1 indicates that the next step is to connect the tibial digitizer 14A to the tibial reference 12, by way of the mating connection (e.g., FIG. 2) therebetween.

As mentioned previously, the positioning of the surgical device 14 may not require the physical interconnection with the surgical device 12. The data on the screen 1 may pertain to the installation of the surgical device 14 at a specific location on the bone A, per surgical technique, for instance at a given distance from the surgical device 12 as detectable by proximity switches and sensors.

Referring to FIG. 4B, the tibial digitizer 14A is matingly connected to the tibial reference 12, resulting in the trigger of the triggered unit 16. Accordingly, if the triggering conditions are met (e.g., time lapsed, proximity, etc.), the CAS processing unit 20 automatically changes the data on the interface 26, as indicated by screen 2 in FIG. 4B. The change of data may be the automatic change of mode in the procedure flow to start gathering data associated with the tibial digitizer 14A (e.g., the registration of a tibial axis), going from a commanding mode to a data-collecting mode. The change of data may also be an indication that the devices 12 and 14 are adequately connected to one another, thereby prompting the operator of the CAS system 10 to perform another step.

The aforementioned steps are part of a complete set of steps, some being mandatory or optional or prerequisites as defined in the surgical technique, operated by the CAS processing unit 20 in accordance with the CAS application 25. The aforementioned steps may be repeated during the surgical procedure. For instance, when installing the cutting block 14B (FIG. 3), the automatic trigger may also cause a change in the surgical procedure flow.

The invention claimed is:

1. A computer-assisted surgery system comprising:
a first surgical device with a tracking unit tracked during a surgical procedure and adapted to perform a first function associated to the surgical procedure;
a second surgical device adapted to perform a second function associated to the surgical procedure;
a triggered unit triggered when the first surgical device and the second surgical device reach a predetermined proximity relation;
a surgical procedure processing unit tracking at least the first surgical device, the surgical procedure processor comprising:
a trigger detector detecting a triggering of the triggered unit;
a computer-assisted surgery application operating steps of a surgical procedure;
a controller for commanding the computer-assisted surgery application to activate a selected step associated with the second function in the surgical procedure when the trigger detector signals a detection; and
an interface for displaying information about the selected step in the surgical procedure.

2. The computer-assisted surgery system according to claim 1, wherein one of the surgical devices has a female connector, another of the surgical devices has a male connector, whereby the surgical devices interconnect in a mating engagement of the male and female connectors.

3. The computer-assisted surgery system according to claim 2, wherein the triggered unit is a switch and the predetermined proximity relation is the mating engagement, whereby the switch is triggered by the mating engagement of the male and the female connector.

4. The computer-assisted surgery system according to claim 1, wherein the first surgical device is a reference tool mounted to the bone for tracking of the bone.

5. The computer-assisted surgery system according to claim 4, wherein the second surgical device is a digitizing tool releasably connected to the reference tool for determining an axis of the bone.

6. The computer-assisted surgery system according to claim 1, further comprising a conditions database in one of the triggered unit and the trigger detector to confirm that the predetermined proximity relation is in accordance with conditions of the conditions database.

7. The computer-assisted surgery system according to claim 1, wherein the selected step is a change of mode, and the interface automatically changes mode when the trigger detector signals a detection.

8. The computer-assisted surgery system according to claim 1, wherein the second surgical device has a tracking unit for being tracked during the surgical procedure.

9. The computer-assisted surgery system according to claim 1, wherein the tracking unit comprises a micro-electromechanical system.

* * * * *